(12) United States Patent
Whalen et al.

(10) Patent No.: US 7,507,394 B2
(45) Date of Patent: *Mar. 24, 2009

(54) HIGH VISCOSITY EMBOLIZING COMPOSITIONS

(75) Inventors: Thomas J. Whalen, Encinitas, CA (US); Chinh N. Tran, Mission Viejo., CA (US); Noah M. Roth, Irvine, CA (US); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 1119 days.

This patent is subject to a terminal disclaimer.

(21) Appl. No.: 10/281,142

(22) Filed: Oct. 28, 2002
(Under 37 CFR 1.47)

(65) Prior Publication Data

US 2003/0099597 A1 May 29, 2003

Related U.S. Application Data

(63) Continuation of application No. 09/574,379, filed on May 19, 2000, now Pat. No. 6,531,111.

(60) Provisional application No. 60/135,288, filed on May 21, 1999.

(51) Int. Cl.
*A61K 49/00* (2006.01)
*A61K 49/04* (2006.01)
*A61L 24/00* (2006.01)
*A61L 27/00* (2006.01)
*A61L 27/38* (2006.01)
*A61L 27/56* (2006.01)
*A61L 24/06* (2006.01)
*A61L 24/04* (2006.01)
*A61L 24/08* (2006.01)
*A61L 24/02* (2006.01)
*A61L 27/58* (2006.01)

(52) U.S. Cl. .............. 424/9.45; 424/9.455; 424/9.4; 424/9.41; 424/9.411; 424/443; 424/426; 424/422; 424/1.65; 604/264; 514/708; 514/546

(58) Field of Classification Search ............... 424/9.45, 424/9.455, 9.4, 9.41, 9.411, 443, 426, 422, 424/1.65; 604/264, 49; 514/708, 546
See application file for complete search history.

(56) References Cited

U.S. PATENT DOCUMENTS 3,527,224 A 9/1970 Rabinowitz (Continued)

FOREIGN PATENT DOCUMENTS

EP 0 291 177 A2 4/1988

(Continued)

OTHER PUBLICATIONS

Dictionary of biochemistry and Molecular Biology, 2nd edition, 1989, p. 262.*

(Continued)

*Primary Examiner*—Shengjun Wang
(74) *Attorney, Agent, or Firm*—Foley & Lardner LLP

(57) ABSTRACT

Disclosed are novel compositions for embolizing blood vessels which are particularly suited for treating vascular lesions via catheter delivery.

17 Claims, 1 Drawing Sheet

U.S. PATENT DOCUMENTS

| | | | |
|---|---|---|---|
| 3,591,676 | A | 7/1971 | Hawkins et al. |
| 4,079,124 | A | 3/1978 | Winchell |
| 4,631,188 | A | 12/1986 | Stoy et al. |
| 4,795,741 | A | 1/1989 | Leshchiner et al. |
| 4,938,763 | A | 7/1990 | Dunn et al. |
| 5,202,352 | A | 4/1993 | Okada et al. |
| 6,017,977 | A | 1/1995 | Evans et al. |
| 5,443,454 | A | 8/1995 | Tanabe et al. |
| 5,580,568 | A * | 12/1996 | Greff et al. ............... 424/423 |
| 5,667,767 | A * | 9/1997 | Greff et al. ............... 424/9.411 |
| 5,695,480 | A * | 12/1997 | Evans et al. ............... 604/264 |
| 5,851,508 | A * | 12/1998 | Greff et al. ............... 424/9.411 |
| 6,051,607 | A * | 4/2000 | Greff ............... 514/546 |
| 6,214,315 | B1 * | 4/2001 | Greff et al. ............... 424/1.25 |
| 6,531,111 | B1 * | 3/2003 | Whalen et al. ............... 424/9.45 |

FOREIGN PATENT DOCUMENTS

| | | |
|---|---|---|
| JP | 5-57014 | 3/1993 |
| JP | 5-253283 | 5/1993 |
| JP | 6-107549 | 4/1994 |
| WO | WO 85/00969 | 3/1985 |
| WO | WO 97/04656 | 2/1997 |
| WO | WO 97/04657 | 2/1997 |
| WO | WO 97/04813 | 2/1997 |
| WO | 00/71196 A1 | 11/2000 |

OTHER PUBLICATIONS

Taki et al. (AJNR 11: 163-168, Jan./Feb. 1990).*

Yamashita, et al. "Characteristics of Ethylene Vinyl Alcohol Copolymer (EVAL) Mixtures", AJNR Am. J. Neuroadiology, 15:1103-1105 (1994).

Casarett and Doull's Toxicology, Amdur et al., Editors, *Toxic Effects of Metals,*4th Ed.:661-664, Pergamon Press, N.Y., N.Y.

Castaneda-Zuniga, et al., *Interventional Radiology*, Vas. Emb.,Part 1, 1:9-32, Williams & Wilkins, Publishers (1992).

Guglielmi, et al., "Electrothrombosis of Saccular Aneurysms Via Endovascular Approach", *J. Neurosurg.*, 75:8-14 (1991).

Kinugasa, et al., "Early Treatment of Subarachnoid Hemorrhage After Preventing Rerupture of an Aneurysm", *J. Neurosurg.*, 83:34-41 (1995).

Kinugasa, et al., "Prophylatic Thrombosis to Prevent New Bleeding and to Delay Aneurysm Surgery", *Neurosurg.*, 36(4):661-667 (1995).

Kinugasa, et al., "Direct Thrombosis of a Pseudoaneurysm After Obliteration of a Cartoid-Cavernous Fistula with Cellulose Acetate Polymer: Technical Case Report", *Neurosurgery*, 35(4):755-760 (1994).

Kinugasa, et al., "Direct Thrombosis of Aneurysms with Cellulose Acetate Polymer, Part II: Preliminary Clinical Experience", *J. Neurosurg.*, 77:501-507 (1992).

Link, et al., "Hydrogel Embolic Agents", *Invest. Radiol.*, 29(8): 746-751 (1994).

Mandai, et al., "Direct Thrombosis of Aneurysms with Cellulose Acetate Polymer, Part I: Results of Thrombosis in Experimental Aneurysms", *J. Neurosurg.*, 77:497-500 (1992).

Miyatake, et al., "Cobb's Syndrome and its Treatment with Embolization", *J. Neurosurg.*, 72:497-499 (1990).

Naitoh, et al., "Removal of Beta-2-Microglobulin by Diffusion Alone is Feasible Using Highly Permeable Dialysis Membranes", *Trans. Am. Soc. Artif. Intern. Organs.*, 630-634 (1988).

Park, et al., "New Polymers for Therapeutic Embolization", Poster #47, Meeting of Radiological Society of North America (1993).

Sadato, et al., "Experimental Study and Clinical Use of Poly(vinyl acetate) Emulsion as Liquid Embolisation Material", *Neuroradiology*, 36:634-641 (1994).

Su, et al., "Histopathological Studies of a New Liquid Embolization Method Using Estrogen-Alcohol and Polyvinyl Acetate", *Surg. Neurol.*, 36: 4-11 (1991).

Sugiu, et al., "Direct Thrombosis of Experimental Aneurysms with Cellulose Acetate Polymer (CAP): Technical Aspects, Angiographic Follow-Up, and Histological Study", *J. Neurosurg.*, 83:531-538 (1995).

Taki, et. al., "A New Liquid Material for Embolization of Arteriovenous Malformations", *Am. J. Neuroradiology*, 11:163-168 (1990).

Taki, et. al., "Selection and Combination of Various Endovascular Techniques in the Treatment of Giant Aneurysms", *J. Neurosurg.*, 77:37-42 (1992).

Taki, et al., "Possibility and Limit of Intravasular Surgery", *Med. Tribune*, pp. 46-47 (1989).

Tereda, et al., "Embolization of Arteriovenous Malformations with Peripheral Aneurysms Using Etheylene Vinyl Alcohol Copolymer", *J. Neurosurg.*, 75:655-660 (1991).

Yamashita, et al., "Characteristics of Ethylene Vinyl Alcohol Copolymer (EVAL) Mixtures", *Am. J. Neuroradiology*, 15:1103-1105 (1994).

* cited by examiner

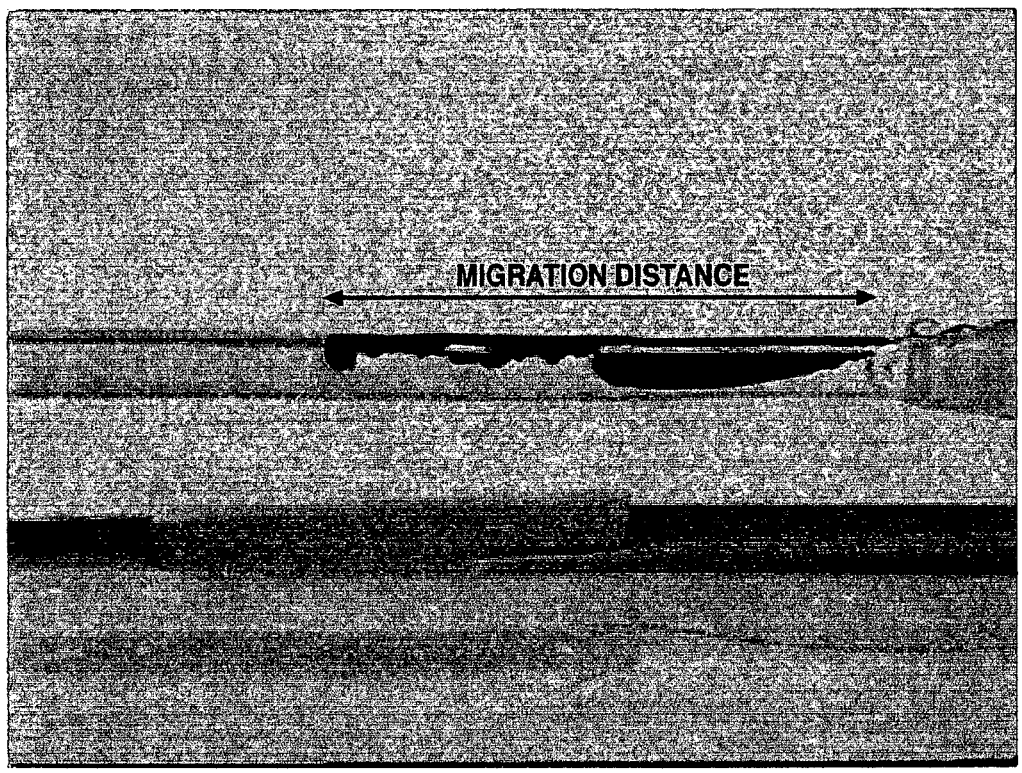
FIG._1
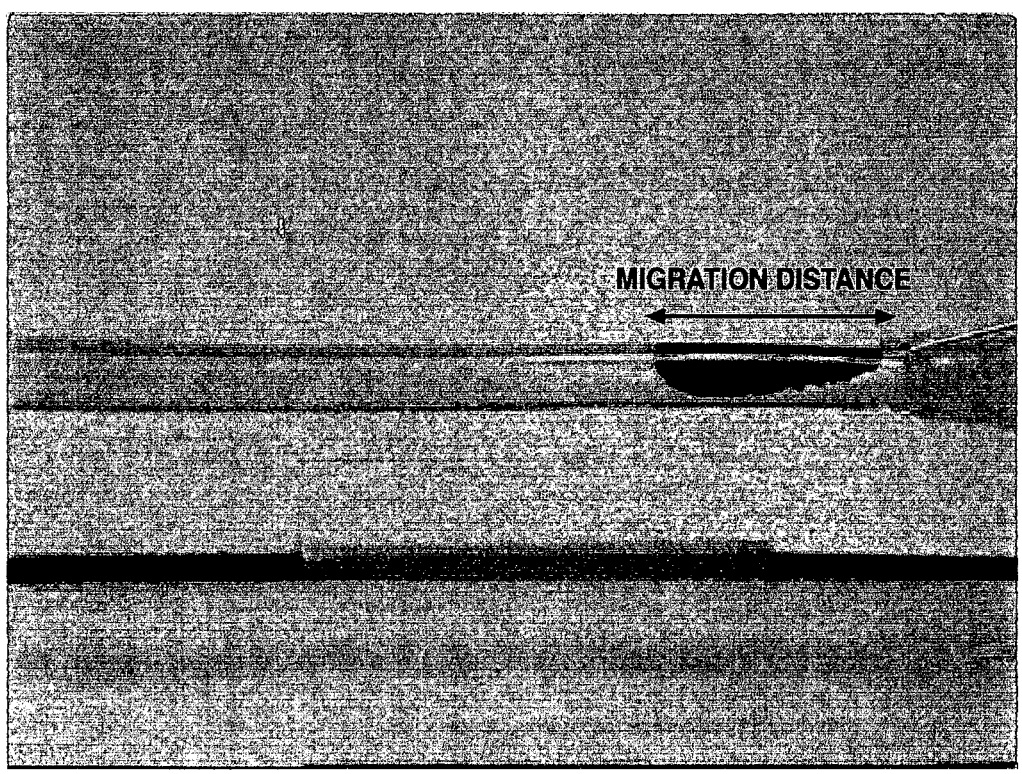
FIG._2

HIGH VISCOSITY EMBOLIZING COMPOSITIONS

CROSS-REFERENCE TO RELATED APPLICATIONS

This application is a continuation application of U.S. patent application Ser. No. 09/574,379, filed May 19, 2000, now U.S. Pat. No. 6,531,111 which claims the benefit of U.S. Provisional Application No. 60/135,288, filed May 21, 1999, which application is incorporated herein by reference in its entirety.

BACKGROUND OF THE INVENTION

1. Field of the Invention

This invention is directed to novel compositions for embolizing blood vessels which are particularly suited for treating aneurysms, arteriovenous malformations (AVMs) at high flow fistulas and embolizing blood vessels.

In one embodiment, the compositions of this invention comprise a biocompatible polymer, a biocompatible solvent and a biocompatible contrast agent wherein the viscosity of the composition is at least about 150 cSt and preferably at least about 200 cSt at 40° C.

2. References

The following publications are cited in this application as superscript numbers:

[1] Mandai, et al., "Direct Thrombosis of Aneurysms with Cellulose Acetate Polymer", *J. Neurosurg.*, 77:497-500 (1992)

[2] Kinugasa, et al., "Direct Thrombosis of Aneurysms with Cellulose Acetate Polymer", *J. Neurosurg.*, 77:501-507 (1992)

[3] Casarett and Doull's *Toxicology*, Amdur et al., Editors, Pergamon Press, New York, pp. 661-664 (1975)

[4] Greff, et al., U.S. Pat. No. 5,667,767 for "Novel Compositions for Use in Embolizing Blood Vessels", issued on Sep. 16, 1997

[5] Greff, et al., U.S. Pat. No. 5,580,568 for "Cellulose Diacetate Compositions for Use in Embolizing Blood Vessels", issued on Dec. 3, 1996

[6] Kinugasa, et al., "Early Treatment of Subarachnoid Hemorrhage After Preventing Rerupture of an Aneurysm", *J. Neurosurg.*, 83:34-41 (1995)

[7] Kinugasa, et al., "Prophylactic Thrombosis to Prevent New Bleeding and to Delay Aneurysm Surgery", *Neurosurg*, 36:661 (1995)

[8] Taki, et al., "Selection and Combination of Various Endovascular Techniques in the Treatment of Giant Aneurysms", *J. Neurosurg.*, 77:37-42 (1992)

[9] Evans, et al., U.S. patent application Ser. No. 08/655,822 for "Novel Compositions for Use in Embolizing Blood Vessels", filed May 31, 1996.

[10] Dunn, et al., U.S. Pat. No. 4,938,763 for "*Biodegradable In-Situ Forming Implants and Methods of Producing Same*", issued Jul. 3, 1990

All of the above references are herein incorporated by reference in their entirety to the same extent as if each individual reference was specifically and individually indicated to be incorporated herein by reference in its entirety.

3. State of the Art

Embolization of blood vessels is conducted for a variety of purposes including the treatment of tumors, the treatment of lesions such as aneurysms, uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuroendovascular intervention including the treatment of otherwise inoperable lesions. Specifically, development of microcatheters and guide wires capable of providing access to vessels as small as 1 mm in diameter allows for the endovascular treatment of many lesions.

Embolizing compositions (embolic compositions) heretofore disclosed in the art include those comprising a biocompatible polymer, a biocompatible solvent and a contrast agent which allowed visualization of the in vivo delivery of the composition via fluoroscopy.[1-8] Such compositions typically contain no more than about 8 weight percent of biocompatible polymer based on the weight of the total composition.

Notwithstanding the benefits associated with the use of such embolic compositions in treating aneurysms and other vascular disorders, in vivo these compositions formed coherent masses which often suffer from solidification and formation of a coherent mass distal from the point of ejection from the catheter. That is to say that upon ejection of the embolic composition in a vascular site, the coherent mass subsequently formed was often distal and not proximate the ejection port of the catheter. Moreover, upon solidification, the solid mass formed was often linear in shape (i.e., having a "string shape").

In many circumstances, a contiguous or ball shape precipitate formed at the ejection port is desired (e.g., to fill an aneurysm). Distal solidification of a string shape precipitate makes site specific delivery of the solid mass in the vasculature difficult. As is apparent, site specific delivery of the solid mass is essential for treatment of vascular disorders such as aneurysms. Solidification at points distal to the ejection port, as is common in string shape precipitates, can result in the solid mass forming not in the aneurysm sac but in the artery attendant the aneurysm. Such a string shape precipitate is more prone to fragmentation which can lead to embolization of this artery and possible incapacitation or death of the patient. Moreover, such fragmentation can lead to particles or fragments being "washed" downstream and lodging at undesired locations in the vasculature.

This invention is based, in part, on the discovery that the formation of a solid non-migratory mass having a substantially contiguous or "ball" shape can be achieved by use of embolic compositions comprising a biocompatible polymer, a biocompatible solvent and optionally a contrast agent wherein the composition has a viscosity of at least about 150 cSt at 40° C. The use of such high viscosity embolic compositions was heretofore not preferred in view of the fact that the viscosity of these compositions is significantly higher than those containing 8 weight percent polymer thereby rendering it difficult to employ conventional delivery means (e.g., syringe) for use in combination with the catheter for the controlled delivery of these compositions in vivo.

However, delivery means such as the threaded syringes described, for example, in U.S. Provisional Patent Application Serial Nos. 60/135,289 and 60/135,287, entitled "THREADED SYRINGE" and entitled "SCREW SYRINGE WITH FORCE RELEASE MECHANISM", both of which were filed on May 21, 1999, now renders the use of these highly viscous compositions practical. Both of these applications are incorporated herein by reference in their entirety.

SUMMARY OF THE INVENTION

This invention is directed to the novel and unexpected discovery that the use of embolic compositions comprising a viscosity of at least about 150 cSt at 40° C. provides for the in vivo formation of a solid, non-migratory mass which mass is substantially contiguous in shape.

Without being limited to any theory, it is now believed that embolic compositions having such a high viscosity permit more rapid and consistent solidification in vivo thereby rendering the solid mass formed non-migratory and substantially contiguous in shape. It is further believed that the rapid and consistent solidification in vivo arises at least in part from the high viscosity of these compositions which renders migration from the ejection port of the catheter at the vascular site more difficult.

Accordingly, in one of its composition aspects, this invention is directed to a composition comprising a biocompatible polymer, a biocompatible contrast agent, and a biocompatible solvent which solubilizes said biocompatible polymer wherein sufficient amounts of said polymer are employed in said composition such that, upon delivery to a vascular site, a polymer precipitate forms which embolizes said vascular site; and further wherein the viscosity of said composition is at least about 150 cSt at 40° C.

In another of its composition aspects, this invention is directed to a composition comprising:

(a) a biocompatible polymer at a concentration of from about 2 to 50 weight percent;

(b) a biocompatible contrast agent at a concentration of from about 10 to about 40 weight percent; and (c) a biocompatible solvent from about 10 to 88 weight percent wherein the weight percent of the biocompatible polymer, contrast agent and biocompatible solvent is based on the total weight of the complete composition; and further wherein the composition has a viscosity of at least about 150 and more preferably at least about 200 cSt at 40° C.

Preferably in this particular composition, the concentration of the polymer ranges from 6 to 50 weight percent and more preferably 8 to 30 weight percent.

In another of its composition aspects, this invention is directed to a composition comprising:

(a) a biocompatible polymer at a concentration of from about 12 to 50 weight percent;

(b) a biocompatible contrast agent at a concentration of from about 10 to about 40 weight percent; and (c) a biocompatible solvent from about 10 to 78 weight percent wherein the weight percent of the biocompatible polymer, contrast agent and biocompatible solvent is based on the total weight of the complete composition and further wherein the composition has a viscosity of at least about 150, preferably at least about 200 and more preferably at least 500 cSt at 40° C.

Preferably the viscosity ranges from about 200 to 40,000 cSt at 40° C., more preferably from about 500 to 40,000 cSt at 40° C. In another embodiment, the viscosity ranges from about 500 to 5000 cSt at 40° C.

In one of its method aspects, this invention is directed to a method for enhancing the formation of a solid, non-migratory coherent mass at a selected vascular site of a mammal which method comprises:

(a) placing a delivery device having an ejection port at a selected vascular site in a mammal;

(b) delivering through the ejection port of the delivery device a composition comprising a biocompatible polymer, a biocompatible solvent and optionally a contrast agent wherein the viscosity of the composition is at least about 150 cSt at 40° C.

Preferably the composition delivered in (b) above comprises a biocompatible polymer, a biocompatible contrast agent and a biocompatible solvent which solubilizes the biocompatible polymer wherein the weight percents of the biocompatible polymer, contrast agent and biocompatible solvent are based on the total weight of the complete composition; further wherein sufficient amounts of said polymer are employed in said composition such that, upon delivery to a vascular site, a polymer precipitate forms which embolizes said vascular site; and still further wherein the viscosity of said composition is at least about 150 cSt at 40° C.

More preferably, the composition delivered in (b) above comprises a a biocompatible polymer at a concentration of from about 2 to 50 weight percent, a biocompatible contrast agent at a concentration of from about 10 to about 40 weight percent, and a biocompatible solvent from about 10 to 88 weight percent wherein the weight percent of the biocompatible polymer, contrast agent and biocompatible solvent is based on the total weight of the complete composition and further wherein the composition has a viscosity of at least about 150 and more preferably at least about 200 cSt at 40° C.

Optionally, prior to the delivering aspect of (b) above, blood flow through the vascular site can be attenuated by insertion of a blood flow attenuating device immediately upstream the ejection port. Such a blood flow attenuating device is preferably an inflatable microballoon which permits both normal and attenuated blood flow depending upon whether the microballoon is deflated or inflated.

The contrast agent is either a water soluble contrast agent or a water insoluble contrast agent. Preferably, the water insoluble contrast agent is a biocompatible material selected from the group consisting of barium sulfate, tantalum powder and tantalum oxide.

In still a further preferred embodiment, the biocompatible solvent is dimethylsulfoxide (DMSO), ethanol, ethyl lactate or acetone.

BRIEF DESCRIPTION OF THE DRAWINGS

FIG. 1 illustrates the migration of the precipitate formed in a tube simulating in vivo conditions during injection of a composition comprising approximately 8.5 weight percent biocompatible polymer and having a viscosity of approximately 90 cSt at 40° C.

FIG. 2 illustrates the migration of the precipitate formed in a tube simulating in vivo conditions during injection of a composition comprising approximately 17 weight percent of the same biocompatible polymer as in FIG. 1 and having a viscosity of approximately 1100 cSt at 40° C.

DETAILED DESCRIPTION OF THE INVENTION

This invention is directed to novel compositions for embolizing blood vessels which are particularly suited for treating vascular lesions via catheter delivery of the composition.

However, prior to discussing this invention in further detail, the following terms will first be defined:

The term "embolizing" refers to a process wherein a material is injected into a blood vessel which, in the case of, for example, aneurysms, fills or plugs the aneurysm sac and/or encourages clot formation so that blood flow into the aneurysm ceases, in the case of high flow AVM's forms a plug or clot to control/reroute blood flow to permit proper tissue perfusion, and, in the case of a vascular site, fills the vascular site to prevent blood flow there through. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art. For example, Dunn, et al.[10] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by the methods of this invention.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to about 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble.

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethyl lactate, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "migration distance" refers to the linear (confluent) distance the solid precipitate forms when 0.1 mL of a composition described herein is injected into an optically clear tube using the test method of Example 3 below. In this example, the migration distance is measured along the length of the precipitation formed as illustrated in FIGS. 1 and 2.

The term "proximate the ejection port" means that the solid coherent mass initially forms at or within about 5 mm of the ejection port. Preferably the solid coherent mass forms within about 3 mm and more preferably within about 1 mm of the ejection port.

Compositions

The polymer compositions employed in this invention are prepared by conventional methods whereby each of the components is added and the resulting composition mixed together until the overall composition is substantially homogeneous.

For example, these compositions can be prepared by adding sufficient amounts of the biocompatible polymer to the biocompatible solvent to achieve the effective concentration for the polymer composition. Preferably, the polymer composition will comprise from about 2 to about 50 weight percent of the biocompatible polymer composition based on the total weight of the polymer composition and more preferably from about 12 to about 50 weight percent. If necessary, gentle heating and stirring can be used to effect dissolution of the biocompatible polymer into the biocompatible solvent, e.g., 12 hours at 50° C. for EVOH being dissolved in DMSO.

The viscosity of the composition is controlled either by the amount of polymer employed and/or its molecular weight. For example, high viscosity compositions which employ low concentrations of polymer can be achieved by use of very high molecular weight biocompatible polymers (e.g., average molecular weight greater than 250,000). Such factors are well known in the art. In any event, the compositions described herein have a viscosity of at least about 150 cSt at 40° C. and preferably at least about 200 cSt at 40° C.

Sufficient amounts of the contrast agent can be added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 weight percent. Insofar as water insoluble contrast agents are not soluble in the biocompatible solvent, stirring is employed to effect homogeneity of the resulting suspension for compositions employing such contrast agents.

In order to enhance formation of the suspension, the particle size of water insoluble contrast agents is preferably maintained at about 10 µm or less and more preferably at from about 1 to about 5 µm (e.g., an average size of about 2 µm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting solution or suspension is conducted as necessary to achieve homogeneity of the composition. Preferably, mixing/stirring of the composition is conducted under an anhydrous atmosphere at ambient pressure. The resulting composition is heat sterilized and then stored preferably in sealed bottles or vials until needed.

Each of the polymers recited herein is commercially available but can also be prepared by methods known in the art. For example, polymers are typically prepared by conventional techniques such as radical, thermal, UV, γ irradiation, or electron beam induced polymerization employing, as necessary, a polymerization catalyst or initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Methods

The compositions described above can then be employed in methods for the catheter assisted embolization of mammalian blood vessels. In such methods, a sufficient amount of this composition is introduced into the selected blood vessel via a catheter delivery means under fluoroscopy so that upon precipitation of the polymer, the blood vessel is embolized. The particular amount of embolic composition employed is dictated by the total volume of the vasculature to be embolized, the concentration of polymer in the composition, the rate of precipitation (solids formation) of the polymer, etc. Such factors are well within the skill of the art.

One particularly preferred method for catheter delivery of the embolic compositions of this invention to the selected vascular site is via a small diameter medical catheter connected to a threaded syringe. One example of a novel threaded syringe has a threaded plunger which is operable as a conventional syringe for aspiration of the embolic composition and then is used in a threaded manner for delivery of the embolic composition. The threaded syringe may also include a tactile or audible indication of delivery which allows clinician to monitor delivery of the embolic composition without looking at the syringe. The catheter for delivery of the embolic compositions preferably has a burst strength of 100 psi or greater, and more preferably 200 psi or greater, and still more preferably 1000 psi or greater. In order to prevent catheter burst, the threaded syringe may be provided with a force release mechanism which prevents the clinician from applying pressures above the catheter burst strength. As an alternative delivery means to the threaded syringe, a syringe pump may be used.

Preferably, in order to enhance the in vivo delivery of a uniform suspension of this composition, the composition is mixed at a temperature of above 40° C. which ensures formation of a uniform suspension and then this heated composition is transferred while maintaining its temperature above room temperature and preferably above 40° C. into the catheter for in vivo delivery.

Specifically, a uniform suspension is achieved by mixing the compositions at a temperature above about 40° C., preferably from above about 40° C. to about 90° C., and more preferably from about 50° C. to about 70° C. The particular temperature employed should be sufficiently high to ensure adequate mixing of the composition.

In a particularly preferred embodiment, the composition is heated for a period of time from at least about 3 to about 20 minutes and preferably from about 5-10 minutes to facilitate formation of a uniform suspension. In some cases, the formation of a uniform suspension requires that the heated composition be placed in a suitable mixer, e.g., vortex mixer, and is mixed until the suspension is homogeneous. In this case, after formation of the homogenous suspension via the mixer, the composition is preferably reheated to a temperature of from above about 40° C. to about 90° C. and preferably from about 50° C. to about 70° C. The specific temperature employed for heating is selected relative to the biocompatible solvent and biocompatible polymer employed. Such selections are well within the skill of the art.

In either case, the heated composition is then transferred preferably via a syringe and delivered into the catheter under conditions wherein the temperature of the composition is above room temperature and preferably above about 40° C. In one preferred embodiment, the conditions which effect such transfer are rapid transfer (e.g., transfer occurs within 2 minutes of heating cessation) of the composition to the catheter.

Surprisingly, the heated composition maintains both a uniform suspension and ease of delivery during catheter injection into a vascular site in a mammal and, when ejected at the distal end of the catheter, there is no evidence of trauma to this site. See, for example, U.S. patent application Ser. No. 09/574,963, now U.S. Pat. No. 6,454,738, filed concurrently herewith and entitled "Methods for Delivering In Vivo Uniform Dispersed Embolic Compositions of High Viscosity" which application is incorporated herein by reference in its entirety.

The particular catheter employed is not critical provided that polymeric catheter components are compatible with the embolic composition (i.e., the catheter components will not readily degrade in the embolic composition). In this regard, it is preferred to use polyethylene in the catheter components because of its inertness in the presence of the embolic composition described herein. Other materials compatible with the embolic compositions can be readily determined by the skilled artisan and include, for example, other polyolefins, fluoropolymers (e.g., Teflon™), silicone, etc.

When delivered by catheter, preferred delivery techniques include those set forth in U.S. Pat. No. 6,645,167, entitled "Methods for Embolizing Vascular Sites With an Embolizing Composition" which is incorporated herein by reference in its entirety.

In another embodiment, the catheter employs an interface device which connects to the syringe to create a blunt interface between a DMSO composition not containing either a biocompatible polymer or a contrast agent and the embolic composition described herein. Such devices are disclosed in U.S. Pat. No. 6,511,472 entitled "Interface Needle and Method for Creating a Blunt Interface Between Delivered Liquids" which is incorporated herein by reference in its entirety.

Utility

The compositions described herein are useful in embolizing mammalian blood vessels which, in turn, can be used to prevent/control bleeding (e.g., organ bleeding, gastrointestinal bleeding, vascular bleeding, bleeding associated with an aneurysm), to ablate diseased tissue (e.g., tumors, etc.), and to treat aneurysms and/or AVMs. Accordingly, these compositions find use in human and other mammalian subjects requiring embolization of blood vessels.

It is contemplated that these compositions can be employed as a carrier for a compatible pharmaceutically active compound wherein this compound is delivered in vivo for subsequent release. Such compounds include, by way of example only, antibiotics, anti-inflammatory agents, chemotherapeutic agents, anti-angiogenic agents, and the like.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeters |
| cSt = | centistokes |
| DMSO = | dimethylsulfoxide |
| EVOH = | ethylene vinyl alcohol copolymer |
| EVOH-1 = | 44 mole percent ethylene/56 mole percent vinyl alcohol having a melt index of about 10 |
| EVOH-2 = | 44 mole percent ethylene/56 mole percent vinyl alcohol having a melt index of about 1.5 |
| EVOH-3 = | 48 mole percent ethylene/52 mole percent vinyl alcohol and a weight average molecular weight (GPC MW) of 136,000 |
| g = | gram |
| mL = | milliliter |
| mm = | millimeter |
| µm = | micron |

Example 1

This example illustrates the effect of polymer concentration on viscosity and the compositions described herein comprise only biocompatible polymer and biocompatible solvent (DMSO). However, the results of this example correlate to the viscosities of compositions further comprising a water insoluble contrast agent since this agent will not have any significant effect on viscosity.

In this example, the recited polymer was added to DMSO and stirred until homogenous. Heating of the solution was employed as required to effect dissolution. Viscosities are measure at 40° C. and are reported in cSt. The results are set forth below (all percents are weight percents based on the polymer and solvent):

| Polymer Type/ Grade | Concentration (% polymer) | Viscosity |
|---|---|---|
| EVOH-1 | 10.00 | 78 |
| EVOH-1 | 16.00 | 346 |
| EVOH-2 | 8.00 | 55 |
| EVOH-2 | 10.00 | 103 |
| EVOH-2 | 16.00 | 472 |
| cellulose diacetate (50,000) | 12.00 | 1355 |
| cellulose diacetate (50,000) | 8.00 | 314 |
| cellulose diacetate (30,000) | 12.00 | 176 |
| cellulose diacetate (30,000) | 8.00 | 56 |

As is apparent, minimal increases in polymer concentration result in very high increases in viscosity.

Example 2

This example illustrates the preparation of compositions of this invention having a high viscosity. Specifically, EVOH polymer compositions were prepared as follows:

Comparative Example A approximately 8.5 weight % EVOH-3
30 weight % micronized tantalum approximately 61.6 weight % DMSO
Viscosity=approximately 90 cSt at 40° C.

Composition of Example 2 approximately 17.5 weight % EVOH
30 weight % micronized tantalum
approximately 52.5 weight % DMSO
Viscosity=approximately 1100 cSt at 40° C.

In each case, after dissolution of the polymer at 50° C. in DMSO with stirring, micronized tantalum (average size 3 μm) was then added. The resulting composition was heated for about 5 minutes at 70° C. then shaken in a vortex mixer for approximately 20 minutes at room temperature to obtain a uniform suspension of the insoluble tantalum in the composition.

Example 3

The purpose of this example is to establish that reduced precipitate migration can be achieved by increasing the viscosity of the polymer composition.

The compositions of Comparative Example A and Example 2 were tested to determine their relative migration distance under approximate in vivo conditions. Specifically, two identical silicone (optically clear) tubes each having an approximate 4 mm lumen were constructed and an aqueous solution of saline at 37° C. was allowed to flow there through at a flow rate of 130 mL/minute and a pressure of approximately 120/80 mm of Hg. The two tubes are labeled Tube A and Tube 2.

The compositions of Comparative Example A and Example 2 were loaded into 2 separate syringes which were labeled Syringe A and Syringe 2. The 21 French needle of Syringe A was inserted confluently into the lumen of Tube A to provide access into the lumen. Similarly, the 21 French needle of Syringe 2 was inserted confluently into the lumen of Tube 2 to provide access into the lumen. The contents of each syringe (approximately 0.1 mL) were then injected confluently with the saline flow into their respective tubes at an injection rate of about 0.12 cc/minute.

Upon injection, each composition formed a solid precipitate in the tube. The degree of migration of the precipitate formed about 1 minutes after start of injection was visually determined through the optically clear walls of the tube. Photographs of the formed precipitate were taken and are reproduced as FIGS. 1 and 2 wherein FIG. 1 illustrates the migration of the precipitate formed during injection of the composition of Comparative Example A and FIG. 2 illustrates the migration of the precipitate formed during injection of the composition of Example 2.

The results of this example illustrate that the composition of Example 2 forms a more "ball-like" precipitate with significantly less migration under identical flow conditions as compared to the precipitate formed from the composition of Comparative Example A. In fact, the composition of Example 2 migrated approximately 40% of that of the composition of Comparative Example A.

Example 4

The purpose of this example is to further demonstrate that reduced migration of the formed precipitate can be achieved by increasing the viscosity of the composition.

Specifically, in this example, different polymer compositions were prepared as described above using three different biocompatible polymers [i.e., polyvinylacetate (PVAc), cellulose acetate butyrate (CAB), or ethylene vinyl alcohol (EVOH)]. The concentration (in weight percent based on the total weight of the composition) and molecular weight of each of the polymers are as defined below and were employed in a composition comprising 30 weight percent of tantalum and the balance being DMSO. As noted above, at the same concentration, a higher molecular weight polymer imparts a higher viscosity to these compositions than the same polymer having a lower molecular weight. Accordingly, internal comparisons of migration distance between similar polymers of different molecular weight effectively determines the effect of viscosity on the migration of the formed precipitate.

In these tests, each of the compositions were tested for average migration distance (average of four runs) in the manner described in Example 3 above with the exceptions that the 21 French needle of each syringe was used to puncture the wall of tube at an angle of about 30° to provide access into the lumen; the average ejection rate was 0.10 cc/minute and the saline flow rate was 300 mL/min.

The results of this analysis are set forth in Tables I-III below:

TABLE I

| Polymer | MW (weight ave. based on GPC) | Concentration (wght. %) | Viscosity (cSt at 40° C.) | Average Migration Distance (in mm) |
|---|---|---|---|---|
| EVOH | 136,360 | 3 | 6 | 28[A] |
| EVOH | 136,360 | 15 | 217 | 18 |
| EVOH | 136,360 | 30 | 2355 | 15 |

TABLE II

| Polymer | MW (weight ave. based on GPC) | Concentration (wght. %) | Viscosity (cSt at 40° C.) | Average Migration Distance (in mm) |
|---|---|---|---|---|
| PVAc | 500,000 | 3 | 16 | 38 |
| PVAc | 500,000 | 15 | 1072 | 28 |
| PVAc | 500,000 | 30 | 21284 | 15 |
| PVAc | 83,000 | 3 | 4 | * |
| PVAc | 83,000 | 15 | 41 | 44 |
| PVAc | 83,000 | 30 | 242 | 38 |
| PVAc | 12,800 | 3 | 2 | * |
| PVAc | 12,800 | 15 | 6 | 41[a] |
| PVAc | 12,800 | 30 | 16 | 51[a] |

TABLE III

| Polymer | MW (number ave.) | Concentration (wght. %) | Viscosity (cSt at 40° C.) | Average Migration Distance (in mm) |
|---|---|---|---|---|
| CAB | 70,000 | 3 | 41 | 23[A] |
| CAB | 70,000 | 15 | 7599 | 16 |
| CAB | 70,000 | 30 | [b] | 11 |
| CAB | 30,000 | 3 | 6 | * |
| CAB | 30,000 | 15 | 155 | 18 |
| CAB | 30,000 | 30 | 1288 | 19 |
| CAB | 12,000 | 3 | 5 | * |
| CAB | 12,000 | 15 | 81 | 25 |
| CAB | 12,000 | 30 | 601 | 17 |

* indicates that the formed precipitate fragmented and did not form a coherent mass.
[A] indicates that these samples fragmented and that the distance of migration is representative
[B] Value not determined The above data indicates that for viscosities at least about 150 cSt at 40° C. and preferably at least about 200 cSt at 40° C., an increase in viscosity correlates with a reduction in migration distance.

The above data further indicates that an increase in concentration of polymer alone without a corresponding increase in viscosity does not provide for reduced migration distances. For example, in Table II, the first and last compositions have approximately equal viscosities but the last composition has a 10 fold higher concentration of polymer. Nevertheless, the latter composition does not reduce the migration distance as compared to the first composition.

Example 5

The purpose of this example is to still further demonstrate that reduced migration of the formed precipitate can be achieved by increasing the viscosity of the composition. The procedures used in this example were similar to those of Example 4.

The results of this test are set forth in Table IV below:

TABLE IV

| Polymer | Concentration (wght. %) | Viscosity (cSt at 40° C.) | Average Migration Distance (in mm)$^z$ | Standard Deviation |
|---------|-------------------------|---------------------------|-----------------------------------------|---------------------|
| EVOH-3  | 4.6                     | 18                        | 33.2                                    | 6.18                |
| EVOH    | 6.2                     | 34                        | 28.2                                    | 4.15                |
| EVOH    | 9.2                     | 90                        | 24.2                                    | 4.92                |
| EVOH    | 12.3                    | 200                       | 24.6                                    | 3.44                |
| EVOH    | 15.4                    | 500                       | 23.2                                    | 2.59                |
| EVOH    | 23.1                    | 2500                      | 20.0                                    | 2.92                |

From the foregoing description, various modifications and changes in the above described methods will occur to those skilled in the art. All such modifications coming within the scope of the appended claims are intended to be included therein.

What is claimed is:

1. A composition capable of embolizing an aneurysm at a vascular site comprising:
   (a) a biocompatible polymer;
   (b) a biocompatible contrast agent wherein a sufficient amount of said contrast agent is employed in said composition to effect visualization in vivo; and
   (c) a biocompatible solvent which solubilizes said biocompatible polymer
   wherein a sufficient amount of said polymer are employed in said composition such that, upon delivery to a vascular site, a polymer precipitate forms which embolizes said vascular site; and
   further wherein the biocompatible polymer has a molecular weight sufficient to impart to the composition a viscosity of at least about 150 cSt at 40° C.

2. A composition capable of embolizing an aneurysm at a vascular site comprising:
   (a) a biocompatible polymer at a concentration of from about 2 to 50 weight percent;
   (b) a biocompatible contrast agent at a concentration of from about 10 to about 40 weight percent; and
   (c) a biocompatible solvent from about 10 to 88 weight percent
   wherein the weight percents of the biocompatible polymer, contrast agent and biocompatible solvent are based on the total weight of the composition; and
   further wherein the biocompatible polymer has a molecular weight sufficient to impart to the composition a viscosity of at least about 150 cSt at 40° C.

3. The composition according to claim 1 or claim 2, wherein said composition has a viscosity of at least about 200 cSt at 40° C.

4. The composition according to claim 3, wherein said composition has a viscosity of at least about 500 cSt at 40° C.

5. The composition according to claim 4, wherein said composition has a viscosity of from about 500 to 5,000 cSt at 40° C.

6. The composition according to claim 1 or claim 2 wherein said composition has a migration distance of less than 25 mm.

7. The composition according to claim 1 or claim 2, wherein the concentration of biocompatible polymer employed in said composition is from 6 to 50 weight percent.

8. The composition according to claim 7, wherein the concentration of biocompatible polymer employed in said composition is from 8 to 30 weight percent.

9. The composition according to claim 1 or claim 2 wherein said biocompatible solvent is selected from the group consisting of ethyl lactate, dimethylsulfoxide, ethanol and acetone.

10. The composition according to claim 9 wherein said biocompatible solvent is dimethylsulfoxide.

11. The composition according to claim 1 or claim 2 wherein said contrast agent is a water insoluble contrast agent.

12. The composition according to claim 11 wherein said water insoluble contrast agent is selected from the group consisting of tantalum, tantalum oxide, tungsten and barium sulfate.

13. The composition according to claim 12 wherein said contrast agent is tantalum.

14. The composition according to claim 1 or claim 2 wherein said contrast agent is a water soluble contrast agent.

15. The composition according to claim 1 or claim 2 wherein said biocompatible polymer is a non-biodegradable, biocompatible polymer.

16. The composition according to claim 15 wherein said non-biodegradable, biocompatible polymer is selected from the group consisting of cellulose acetates, ethylene vinyl alcohol copolymers, hydrogels, polyacrylonitrile, polyvinylacetate, cellulose butyrate, nitrocellulose, copolymers of urethane/carbonate, copolymers of styrene/maleic acid, and mixtures thereof.

17. The composition according to claim 16 wherein said biocompatible polymer is an ethylene vinyl alcohol copolymer.

* * * * *